United States Patent [19]

Levenson et al.

[11] Patent Number: 4,962,029
[45] Date of Patent: Oct. 9, 1990

[54] COVALENT OLIGONUCLEOTIDE-HORSERADISH PEROXIDASE CONJUGATE

[75] Inventors: Corey Levenson, Oakland; Chu-an Chang, El Cerrito, both of Calif.; Fred T. Oakes, Rochester, N.Y.

[73] Assignee: Cetus Corporation, Emeryville, Calif.

[21] Appl. No.: 437,311

[22] Filed: Nov. 16, 1989

Related U.S. Application Data

[63] Continuation of Ser. No. 103,978, Oct. 2, 1987, abandoned.

[51] Int. Cl.$^5$ ............................ C12N 9/08; C12Q 1/28
[52] U.S. Cl. ........................................ 435/192; 435/6; 435/7; 435/28; 435/188
[58] Field of Search ................... 435/6, 7, 28, 188, 192

[56] References Cited

U.S. PATENT DOCUMENTS 4,626,501 12/1986 Landes ..................................... 435/6
4,657,853  4/1987 Freytag et al. ......................... 435/7
4,670,379  6/1987 Miller ...................................... 435/6

FOREIGN PATENT DOCUMENTS 0124221  7/1984 European Pat. Off. .
0175560  3/1986 European Pat. Off. .
0202758 11/1986 European Pat. Off. .

OTHER PUBLICATIONS

PCT Search Report issued Jan. 27, 1989.
Patent abstracts of Japan 7:(268):C197.
Jablonski, E. et al., *Nucleic Acids Research* 14:6115-6128 (1986).
Renz, M. et al., *Nucleic Acids Research* 12:3435-3445 (1984).
Ruth, J. et al., *Nucleosides & Nucleotides* 6:(1&2):541-542 (1987).
Beaucage, S. et al., *Tetrahedron Lett.* 22:1859-1862 (1981).
Connolly, B., *Nucleic Acids Research* 15:3131-3139 (1987).
Connolly, B., *Nucleic Acids Research* 13:4485-4502 (1985).

*Primary Examiner*—Robert A. Wax
*Attorney, Agent, or Firm*—Dianne E. Reed; Kevin R. Kaster; Albert P. Halluin

[57] ABSTRACT

Oligonucleotides derivatized to incorporate horseradish peroxidase (HRP) are useful in diagnostic methods and provide significant advantage over radioactively labeled oligonucleotide probes. The HRP-derivatized oligonucleotides can be easily and efficiently prepared by reacting a sulfhydryl containing oligonucleotide with a conjugate of a mal-sac-HNSA ester and HRP under mild and easily controlled reaction conditions.

8 Claims, No Drawings

COVALENT OLIGONUCLEOTIDE-HORSERADISH PEROXIDASE CONJUGATE

This application is a continuation of application Ser. No. 103,978, filed Oct. 2, 1987, now abandoned.

BACKGROUND OF THE INVENTION

1. Technical Field

The present invention relates generally to DNA hybridization probes, and more particularly relates to a stable, covalent conjugate of an oligonucleotide and horseradish peroxidase (HRP).

2. Description of the Prior Art

Non-isotopically labelled synthetic DNA fragments have found broad application in molecular biology—e.g., in the areas of DNA sequencing, DNA probe-based diagnostics, and the like. The conjugate disclosed herein is prepared using reagents which facilitate the labeling of oligonucleotides with specific groups by incorporating one or more modifiable sulfhydryl groups at one or more hydroxyl sites within the oligonucleotide. These "functionalizing" reagents are described in co-pending application Serial No. 104,200, of common inventorship and entitled "Oligonucleotide Functionalizing Reagents and Methods", filed on even date herewith. The disclosure of that application is hereby incorporated by reference in its entirety.

Methods of introducing a sulfhydryl group at the 5' terminus of synthetic oligonucleotides are known. For example, Connolly, in Nuc. Acids Res. 13(12) 4485–4502 (1985) and in Nuc. Acids Res. 15(7):3131–3139 (1987), describes a method of incorporating a sulfhydryl moiety into synthetic DNA using S-trityl-0-methoxymorpholinophosphite derivatives of 2-mercaptoethanol, 3-mercaptopropan-1-ol and 6-mercaptohexan-1-ol—i.e., reagents given by the formula

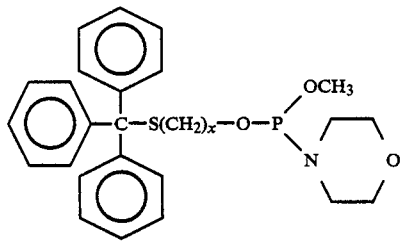

(1)

where x is 2, 3 or 6. Connolly further describes derivatization of the sulfhydryl-containing oligonucleotides with thiol-specific probes.

However, this and other prior art methods suffer from a number of disadvantages as discussed in co-pending application Serial No. 104,200, incorporated by reference above.

As discussed therein, there is a need in the art for oligonucleotide functionalizing reagents which address those considerations. The present invention is directed to a method of "derivatizing" the sulfhydryl-functionalized oligonucleotides described in application Ser No. 104,200, supra, give covalent HRP conjugates.

Covalent conjugates of oligonucleotides and labelling enzymes have been described in the literature. For example, Jablonski et al., in Nuc. Acids Res. 14(15):6115–6128 (1986), describe covalent conjugates of alkaline phosphatase and oligonucleotides prepared using the homobifunctional reagent disuccinimidyl suberate. Renz and Kurz, in Nuc. Acids Res. 12(8):3435–3445 (1984), describe a covalent complex of HRP and oligonucleotides using a polyethyleneimine spacer chain having a molecular weight of about 1400. Also, Ruth and Jablonski, in Nucleosides and Nucleotides 6(1&2):541–542 (1982), disclose conjugates of oligodeoxynucleotides and alkaline phosphatase having a 19-atom spacer chain between the oligomer and the enzyme. While these probes have been used successfully, it would nevertheless be desirable to provide probes which are more stable and which generate color faster, thus yielding a more effective and more readily monitorable means of detection.

SUMMARY OF THE INVENTION

It is accordingly a primary object of the present invention to provide a stable, readily monitorable, "derivatized" oligonucleotide which comprises a sulfhydryl functionalized oligonucleotide covalently conjugated to HRP.

It is a further object of the present invention to provide a method of making such covalent conjugates.

It is another object of the invention to provide a method of using these conjugates in DNA probe-based applications.

Additional objects, advantages and novel features of the invention will be set forth in part in the description which follows, and in part will become apparent to those skilled in the art on examination of the following, or may be learned by practice of the invention. The objects and advantages of the invention may be realized and attained by means of the instrumentalities and combinations particularly pointed out in the appended claims.

In a preferred embodiment of the invention, oligonucleotide functionalizing reagents are used to functionalize an oligonucleotide chain at a hydroxyl group contained therein to introduce a sulfhydryl group. The coupling reaction is effected using standard techniques for coupling a phosphoramidite to a hydroxyl group of an oligonucleotide, as described in co-pending application Ser. No. 104,200, cited supra. After functionalization, the oligonucleotide is derivatized at the new sulfhydryl site with HRP as will be described.

DETAILED DESCRIPTION OF THE INVENTION

1. Definitions

"Sulfhydryl functionalizing" or simply "functionalizing" as used herein means incorporating a protected or unprotected sulfhydryl moiety into an oligonucleotide chain. The sulfhydryl group introduced by functionalization is spaced apart from the oligonucleotide chain by a spacer chain as will be described herein.

"Derivatizing" as used herein means reacting a functionalized oligonucleotide at the added sulfhydryl group with a detectable species, i.e., one that serves as a label in probe-based applications. A "derivatized" oligonucleotide is thus one that is detectable by virtue of the "derivatizing" species. As noted above, the derivatizing species herein is the enzyme horseradish peroxidase.

An "oligonucleotide" as used herein is a single-stranded or double-stranded, typically a single-stranded, chain of nucleotide, typically deoxyribonucleotide, monomer units. While the reagents and methods of the present invention may be used in conjunction with a single nucleotide monomer or with a full-length DNA strand, the "oligonucleotides" herein are typically single-stranded and of from about 2 to about 400 monomer units, and, more typically for most probe-based applications, from about 2 to about 100 monomer units. Optimal length for use as an allele-specific oligonucleotide (or "ASO") is about 13–21 base pairs.

Use of the derivatized oligonucleotides in "probe-based" applications is intended to mean use of the labelled chain to detect or quantify oligonucleotide segments or sequences in a specimen.

A free sulfhydryl group that is "protected" is one that has been reacted with a protecting moiety such that the resulting protected group will not be susceptible to any sort of chemical reaction during the synthetic step or steps during which the protecting group is present.

By "stability" of the functionalized or derivatized oligonucleotide chain is meant substantial absence of steric interference as well as chemical stability under the conditions of most probe-based applications.

By "lower alkyl" and "lower alkoxy" are meant alkyl and alkoxy substituents, respectively, having from about 1 to 6, more typically from about 1 to 3, carbon atoms.

2. Structure of the Functionalizing Reagents

As noted in co-pending application Ser. No. 104,200, incorporated supra, the sulfhydryl functionalizing reagents are substantially linear reagents having a phosphoramidite moiety at one end linked through a hydrophilic spacer chain to an opposing end provided with a protected or unprotected sulfhydryl moiety. These functionalizing reagents are given by the structure

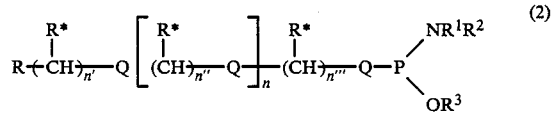

wherein:

R is a protected or unprotected sulfhydryl moiety;

R* is a hydrogen, —CH$_2$OH, or a substituent having the formula

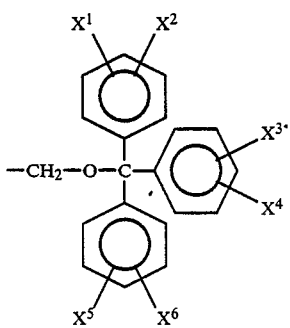

in which X$^1$, X$^2$, X$^3$, X$^4$, X$^5$ and X$^6$ may be the same or different and are selected from the group consisting of hydrogen, lower alkyl and lower alkoxy;

R$^1$ and R$^2$ are independently selected from the group consisting of hydrogen and lower alkyl;

R$^3$ is β-cyanoethyl or methyl;

the Q moieties are selected from the group consisting of

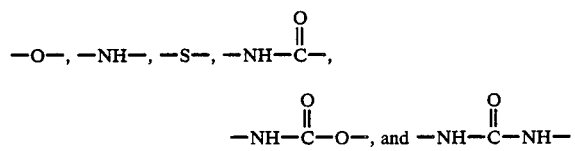

and may be the same or different;

n', n'' and n''' are integers in the range of 2 and 10 inclusive; and n is an integer in the range of 2 and 30 inclusive.

Formula (4) represents one example of a particularly preferred embodiment

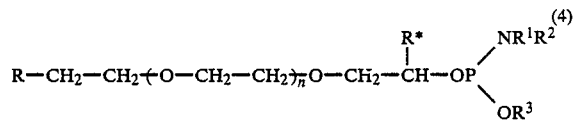

where R, R*, R$^1$, R$^2$, R$^3$ and n are as given above. The hydrophilic spacer chain in such a case is a polyether linkage, e.g., as shown, formed from polyethylene glycol. (In other embodiments encompassed by general structure (2), the spacer chain may also be formed from polypropylene glycol or the like, or from poly(oxyalkyleneamines) such as the Jeffamines ™ sold by Texaco Chemical Co.)

When it is desired to couple the functionalizing reagent to an oligonucleotide chain, at any position, generally, that a nucleoside phosphoramidite could be coupled to the chain, the R moiety is a protected sulfhydryl moiety. The protecting group is selected so that the sulfhydryl moiety remains intact during the phosphoramidite coupling step--i.e., in which the phosphoramidite group of the reagent reacts with the hydroxyl moiety on the oligonucleotide chain. The conditions for this reaction are those used in the conventional method of synthesizing DNA via the so-called "phosphoramidite" route, described, for example, in Beaucage and Caruthers, *Tetrahedron Lett.* 22:1859–1862 (1981).

Examples of particularly preferred sulfhydryl protecting groups are given by R=

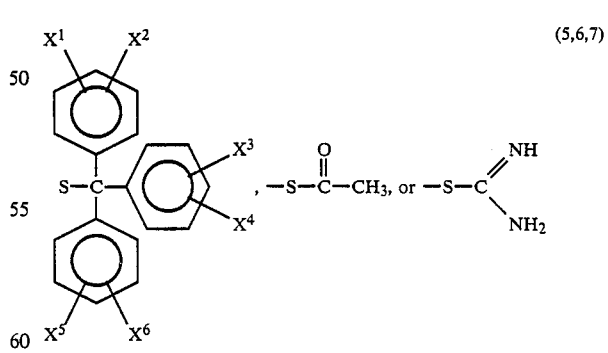

It is to be understood that the aforementioned exemplary protecting groups are illustrative only, and that any number of sulfhydryl protecting groups may be used so long as the above-described "protecting" criteria are met.

The opposing, second end of the functionalizing reagent defined by the phosphoramidite group

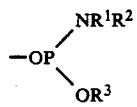

(8)

is selected so as to couple, typically, to the terminal 5' hydroxyl of a growing or completed oligonucleotide chain. As noted above, $R^1$ and $R^2$ are either hydrogen or lower alkyl, and may be the same or different; in a particularly preferred embodiment, both $R^1$ and $R^2$ are isopropyl. $R^3$ is either methyl or $\beta$-cyanoethyl; in a particularly preferred embodiment, $R^3$ is $\beta$-cyanoethyl. Use of the phosphoramidite group as a coupling means is well known in the art of DNA synthesis, and reference may be had to Beaucage and Caruthers (1981), supra, for further description on point.

The spacer chain (9)

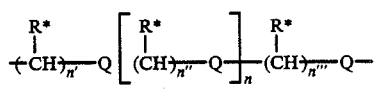

(9)

is a hydrophilic chain wherein n, n', n" and n''' are integers having values as set forth above.

In the preferred embodiment represented by formula (4), the spacer chain is the polyether moiety

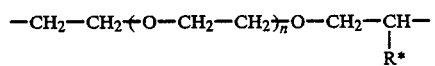

(10)

wherein n is typically 2-30, more typically 2-20 (in some cases, however, n may be larger than 30, i.e., where increased distance is desired between the derivatizing moiety and the oligonucleotide chain). Optimal values for n provide the spacer chain with a total of at least about 8 carbon atoms along its length. The length of the spacer chain is quite relevant to the effectiveness of the reagents, as providing greater distance between the sulfhydryl group and the oligonucleotide chain: (1) facilitates coupling of the reagent to DNA; (2) avoids steric interference which would hinder hybridization and destabilize the functionalized or derivatized oligonucleotide chain; (3) simulates a "solution" type environment in that freedom of movement of the derivatized sulfhydryl moiety is enhanced; and (4) avoids interference with the activity of the derivatizing species, in this case the enzymatic activity of horseradish peroxidase. The hydrophilicity of the spacer chain also enhances the solubility of the functionalized or derivatized oligonucleotide chains in aqueous media.

$R^*$ is either hydrogen, hydroxyl, or the aromatic substituent given by (3) Where $R^*$ is (3), it is selected so that the chromogenic cation

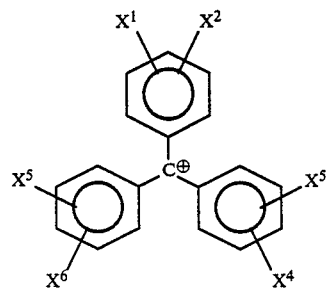

(11)

is monitorable upon release. That is, after coupling of the functionalizing reagent to DNA, deprotection will yield cation (11) in solution. An example of a particularly preferred substituent is dimethoxytrityl (DMT)—i.e., $R^*$ is $-CH_2-O-DMT$.

While in a preferred embodiment, as illustrated by structures (2) and (4), $R^*$ is bonded to the carbon atom adjacent to the phosphoramidite group, it is also possible that $R^*$ may be bonded to one or more other carbon atoms along the spacer chain, as illustrated by formula (2).

3. Use of the Novel Reagents to Functionalize Oligonucleotide Chains

In general, the coupling reaction between the functionalizing reagents and a hydroxyl-containing compound may be represented by the following scheme:

(Scheme I)

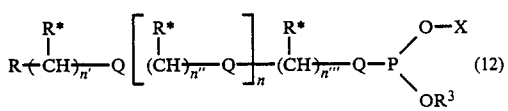

(12)

In Scheme I, X is typically an oligonucleotide chain. The reaction conditions are the same as those used in the phosphoramidite route to DNA synthesis, as noted earlier and as described, inter alia, by Beaucage and Caruthers (1981), supra.

Compound (12) is deprotected as follows. Where $R^*$ is given by formula (3), conversion to an unprotected hydroxyl group is carried out by treatment with acid. The protected sulfhydryl moiety at R may be deprotected with, e.g., silver nitrate.

Multiple functionalization of an oligonucleotide is possible by making use of multiple $R^*$ sites where $R^*$ is $-CH_2OH$ or given by formula (3). After acid deprotection, further functionalization by reaction at the deprotected hydroxyl site is enabled. Thus, in the case of functionalized oligonucleotide (13), for example,

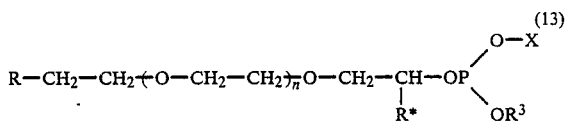

(13)

deprotection of $R^*$ and further functionalization at the $-CH_2OH$ moiety so provided, using a standard phosphoramidite coupling procedure, gives the compound of formula (14)

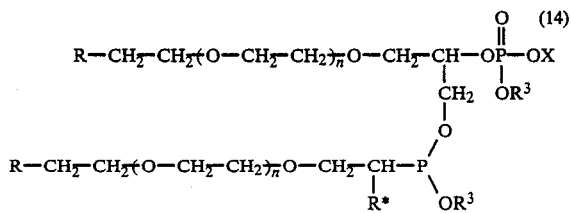

Multiple functionalization at a plurality of hydroxyl groups along an oligonucleotide chain is also possible using the same chemistry.

4. Synthesis of the Novel Reagents

The inventors herein have developed various routes to the novel reagents which are described, in detail in co-pending application Ser. No. 104,200, incorporated by reference hereinabove.

5. Derivatization with HRP

The functionalized oligonucleotide chains prepared using the above-described reagents are primarily useful in probe-based applications. That is, the primary purpose of introducing a sulfhydryl group into an oligonucleotide chain is to enable derivatization at that site with a labeled species. The present application is directed to derivatization with the enzyme horseradish peroxidase.

The derivatized oligonucleotides of the present invention are conjugates comprising an oligonucleotide chain covalently coupled to HRP, the conjugates given by the structure (15)

wherein
R* is hydrogen or —CH₂OH;
the Q moieties are selected from the group consisting of

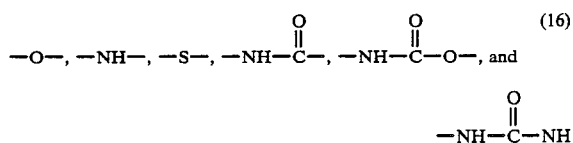

and may be the same or different;
n', n" and n'" are integers in the range of 2 and 10 inclusive;
n is an integer in the range of 2 and 30 inclusive; and
X is an oligonucleotide chain.

The length of the oligonucleotide chain is typically in the range of about 2 and 100 monomer units. Where the conjugate is to be used as an ASO, as noted earlier, the number of monomer units in the chain is preferably about 13–21.

In an exemplary embodiment, the conjugates of the invention may be represented by the structure (17)

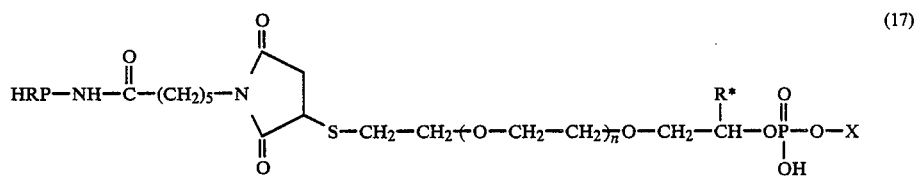

where R*, X and n are as given above. The conjugates of formula (17) result from coupling of exemplary sulfhydryl functionalizing reagent (4) to oligomer X.

The covalent conjugates represented by Formula (15) are prepared by the procedure illustrated in Scheme II:

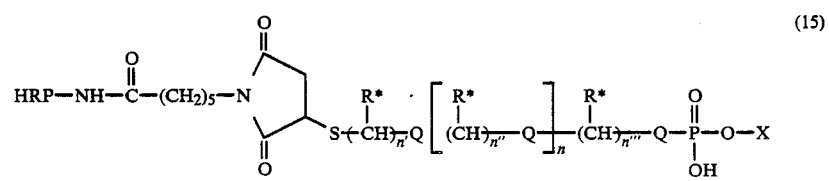

Scheme II

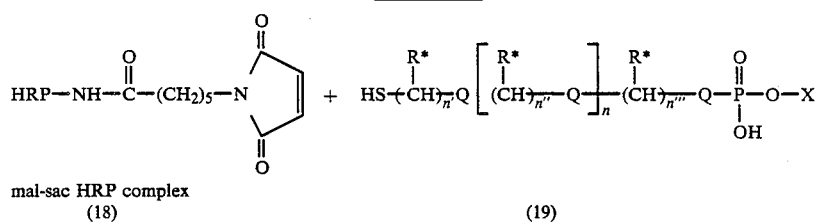

mal-sac HRP complex
(18)

(19)

Scheme II

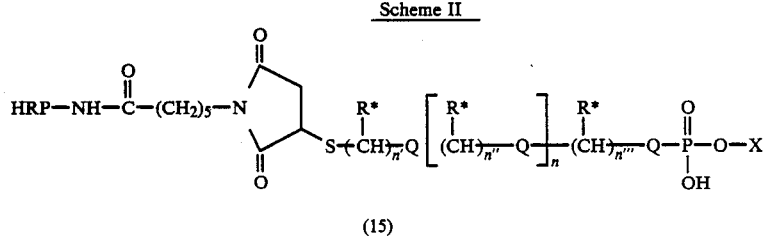

(15)

Preparation of mal-sac-HNSA, i.e., the (N-maleimido-6-aminocaproyl [mal-sac] derivative of 4-hydroxyl-3-nitrobenzene sulfonic acid sodium salt [HNSA]) and the corresponding mal-sac HRP complex (18) is described in co-pending applications Ser. Nos. 637,904 and 839,447, the disclosures of which are incorporated by reference herein. See also Examples 2 and 3 below.

Thiolated oligonucleotide (19) is prepared as described in co-pending application Ser. No. 104,200, previously incorporated by reference. Typically, the tritylthio oligonucleotides are detritylated to reagent (19) just prior to use in the reaction of Scheme II.

The mal-sac HRP complex (18) is coupled to thiolated oligonucleotide (19) by simple admixture, preferably at room temperature or lower. The reaction mixture is allowed to remain at low temperature—e.g., about 0° C.—at least overnight and preferably at least about several days, at which point the covalent HRP conjugate (15) is isolated and purified, preferably chromatographically.

Prior to use in probe-based applications, the conjugates are stored in a phosphate buffer (added salts optional) maintained at a pH of from about 5.5 to about 7.5, preferably about 6.0, at a temperature of from about −10° C. to about 30° C. (with the proviso that the solution not be frozen), optimally about 4° C.

For use in hybridization, the conjugate solutions are normally diluted (the final concentration varying depending on use) with hybridization buffer and used according to standard hybridization techniques (see, e.g., Maniatis, et al., *Molecular Cloning*, New York: Cold Spring Harbor Laboratory, 1982). The general procedure followed is well known in the art, and typically involves: (1) providing a covalent conjugate according to the invention, which conjugate includes an oligomer having a nucleotide sequence substantially complementary to that of an analyte of interest, i.e., sufficiently complementary to enable hybridization; (2) contacting, in solution, the analyte of interest with the covalent conjugate; and (3) detecting the presence of nucleic acid complexes which form by assaying for HRP activity.

Generally, the covalent conjugate hybridizes to an analyte that is attached to a solid support and is then detected thereon.

In sum, the advantages of the novel HRP conjugates in probe-based applications are many. A primary advantage is the relatively long, hydrophilic spacer chain which provides an optimum distance between the HRP and the oligonucleotide, ensuring that full biological activity of the HRP is retained and enhancing the effectiveness of hybridization. The novel conjugates, by virtue of the "R*" moiety, also allow multiple derivatization of one oligonucleotide, i.e., attachment of two or more "spacer-HRP" chains either linked end-to-end, bound at various points within an oligonucleotide chain, or both. Finally, in contrast to other enzyme/oligomer conjugates, e.g., alkaline phosphatase systems, ease of detection is enhanced by the rapid generation of color.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

(a) Synthesis of

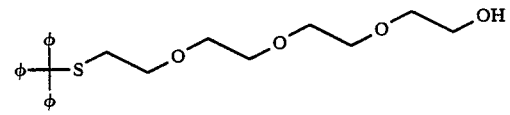

was carried out as follows. To a 0° C. solution of triphenylphosphine (7.87 g; 30 mmole) in 75 mL dry THF was added the diisopropyl azodicarboxylate $(NCOOCH(CH_3))_2$ (6.07 g; 30 mmole) with stirring. After one hour, a solution of tetraethylene glycol (5.83 g; 30 mmole) in 10 mL dry THF was added. All material dissolved to give a pale yellow solution. After one hour, a solution of the mercaptan $\phi_3C$-SH in 20 mL dry THF was added dropwise with cooling and stirring. The reaction mixture was stirred overnight and the solvent removed under reduced pressure. The residue was applied to an $SiO_2$ column and fractionated using methylene chloride followed by a mixture of mixture of methylene chloride and $CH_3CN$ (2:1). The material was rechromatographed on $SiO_2$ using $CH_3CN$ as eluant, and the product was removed from $\phi_3P=O$ by taking small (approximately 15 mL) fractions. The fractions were pooled, yielding 5.22 g (11.53 mmole; 38.4% overall; 77% of theoretical). Elemental analysis was as follows. Calc.: C, 71.65; H, 7.12; S, 7.08. Found: C, 71.32; H, 7.21; S, 7.15.

(b) Preparation of the phosphoramidite:

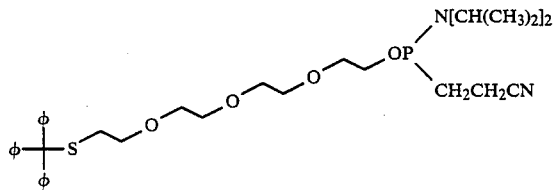

The product obtained in step (a) (4.22 g; 9.30 mmole) was dissolved in 10 mL of acid-free chloroform and placed in a 250 mL round bottom flask preflushed with dry argon. To this solution (.72 g, 5.6 mmole) of [(CH₃)₂-CH]₂-N-Et was added. Then, the phosphoramidite

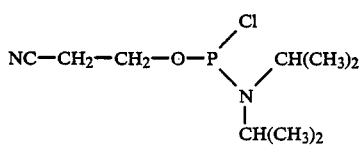

(0.66 g; 2.8 mmole) was added with a syringe over a two-minute period. The reaction was carried out at room temperature and under argon. After one hour, the mixture was transferred with 50 mL of ethyl acetate in a 250 ml separatory funnel and extracted with saturated NaCl solution four times. The organic layer was dried over Na$_2$SO$_4$ and evaporated down to an oily residue under vacuum. This residue was chromatographed with 1% Et$_3$N in ethyl acetate.

EXAMPLE 2

Preparation of mal-sac-HNSA Ester

One molar equivalent (2.24 g) of 4-hydroxy-3-nitrobenzene sulfonic acid sodium salt (HNSA) was mixed together with one molar equivalent (2.06 g) of dicyclohexylcarbodiimide and one molar equivalent (2.10 g) of N-maleimido-6-aminocaproic acid in 25 mL of dimethylformamide (DMF) at room temperature overnight. A white precipitate of dicyclohexylurea was formed. The precipitate was filtered and 300 mL diethyl ether was added to the mother liquor. After about 10 minutes to 4 hours a gummy solid precipitated from the mother liquor. This solid was found to contain 58% of active HNSA ester and 42% of free HNSA.

The analysis consisted of dissolving a small amount of the precipitate in 10 mM phosphate buffer at pH 7.0 and measuring absorbance at 406 nm; this reading provides the amount of unreacted free HNSA which is the contaminating material in the crude HNSA ester. Addition of very small amounts of concentrated strong base (5N NaOH) hydrolyzed the ester. A second reading was taken. Subtraction of the first reading from the second yielded the amount of ester in the original material. For purification purposes, the solid was dissolved in DMF, placed on a LH20 Sephadex ™ gel filtration column and eluted with DMF so that the ester was separated from the contaminating free HNSA. The progress of purification was monitored by thin layer chromatography using chloroform, acetone and acetic acid (6:3:1 v:v:v) as eluting solvent. The product was positively identified as mal-sac HNSA ester by its reactivity with amines. The yield of crude ester produced was estimated to be approximately 30% of theoretical; the purified material consisted of 99% ester.

The ester thus obtained was found to dissolve fully in water and was found to be stable in water for several hours, provided no nucleophiles were added. The purified ester was found to be stable for extended periods when stored desiccated.

EXAMPLE 3

Preparation of Conjugate of mal-sac HNSA Ester and Horseradish Peroxidase (HRP)

An amide of mal-sac HNSA ester and HRP was prepared as follows:

A total of 40 mg (1.0 μmoles) of HRP (Sigma Chemical Co.) was dissolved in 0.5 mL of 0.1 M phosphate buffer at pH 7.0 to yield a total amine concentration of $3.7 \times 10^{-3}$ M. Then, 5 mg ($1.1 \times 10^{-5}$ moles) of the malsac HNSA ester of Example 1A, calculated from the data in Example 2A, was dissolved in 0.5 mL of the HRP solution. The mixture was stirred at room temperature, and the HRP fraction (2.8 mL) was collected on a Pharmacia G-25 column using 0.1 M phosphate buffer, pH 6.0, as eluant.

EXAMPLE 4

Preparation of HRP-Oligonucleotide Conjugates

A thiol-functionalized oligomer was prepared using the following 19-mer which had been synthesized on a Biosearch 8600 DNA Synthesizer: d(TGTTTGCCTGTTCTCAGAC).

The sulfhydryl functionalizing reagent obtained in Example 1(b) was mixed with a solution of the oligomer and coupled thereto under standard phosphoramidite coupling conditions (see, e.g., Beaucage and Caruthers (1981), supra).

The tritylthio oligomer was purified by a standard chromatographic technique using a preparative PRP-1 column and the following solvent gradient (wherein solvent "A" designates CH$_3$CN and "B" designates 5% CH$_3$CN in 0.1M TEAA, pH 7.3) (1) A, 10% →40%, 15 min.; (2) A, 40% →100%, 15 min.; and (3) A, 100%, 5 min. The tritylthio oligomers eluted after about 20 minutes.

The purified tritylthio oligomer so obtained was detritylated using silver nitrate and dithiothreitol (0.1 M and 0.15 M, respectively, in 0.1 M TEAA, pH 6.5). The ditritylated oligomer was then passed through a G-25 (NAP-10) column, concentrated under vacuum to approximately 100 μl, and used right away in the following conjugation reaction.

The mal-sac HRP complex prepared in Example 3 (700 μl) was aliquoted into the thiooligomer to give a final volume of 800 μl. The individual reaction vessels were allowed to remain at room temperature for approximately one hour, and then at about 4° C. for two days, which point the four conjugates were removed and purified on a Nucleogen ™ Deae weak anion exchange column using the following solvent gradient ("B" designates 20 mM Na$_2$PO$_4$, pH 6; "C" designates 20 mM Na$_2$PO$_4$+1 M NaCl, pH 6): (1) B, 0→100%, 30 min.; (2) C, 100%, 10 min.; and (3) C, 100→0%, 5 min. Remaining unconjugated HRP and oligomer eluted after about 2 and about 15-40 min. (depending on the size of the oligomer), respectively, while the conjugate eluted after about 15-40 min as well (also depending on the size of the oligomer). The identity of the product was confirmed by ultraviolet spectroscopy, monitoring peak absorbances of the oligomer (at 260 nm) and of the heme group of HRP (at 402 nm).

We claim:

1. A covalent conjugate of an oligonucleotide chain and horseradish peroxidase given by the structure

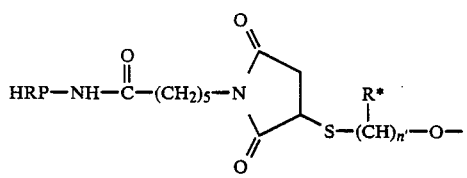

-continued

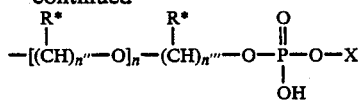

wherein
R* is hydrogen or —CH₂OH;
n′, n″ and n‴ are integers in the range of 2 and 10 inclusive;
n is an integer in the range of 2 and 30 inclusive; and
X is an oligonucleotide chain.

2. The conjugate of claim 1, wherein R* is hydrogen.

3. The conjugate of claim 1, which is useful as an allele-specific oligonucleotide and wherein the oligonucleotide chain is from about 13 to about 21 monomer units in length.

4. A covalent conjugate of an oligonucleotide chain and horseradish peroxidase given by the structure

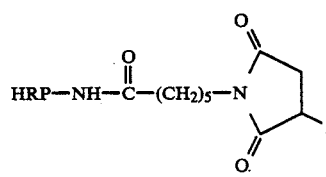

wherein
R* is hydrogen or —CH₂OH;
n is an integer in the range of 2 and 20 inclusive; and
X is an oligonucleotide chain.

5. The conjugate of claim 4, wherein R* is hydrogen.

6. The conjugate of claim 4 which is useful as an allele-specific oligonucleotide and wherein the oligonucleotide chain is from about 13 to about 21 monomer units in length.

7. A method of preparing a covalent conjugate of an oligonucleotide chain and horseradish peroxidase, the conjugate given by the structure

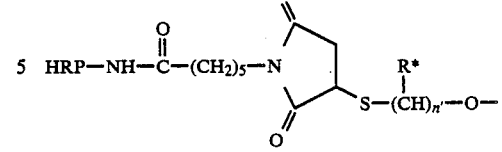

wherein
R* is hydrogen or —CH₂OH;
n′, n″ and n‴ are integers in the range of 2 and 10 inclusive;
n is an integer in the range of 2 and 30 inclusive; and
X is an oligonucleotide chain wherein the method comprises the steps of:
reacting a functionalized oligonucleotide chain having the structure

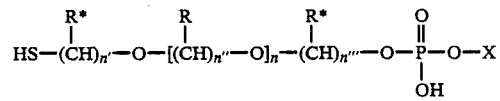

with a conjugate of a mal-sac-HNSA ester and HRP by mixing said conjugate with said functionalized oligonucleotide chain and incubating the mixture at a temperature ranging from about 4° C. to about room temperature for a time ranging from about one hour to about two days.

8. The method of claim 7, wherein the functionalized oligonucleotide chain is given by the structure

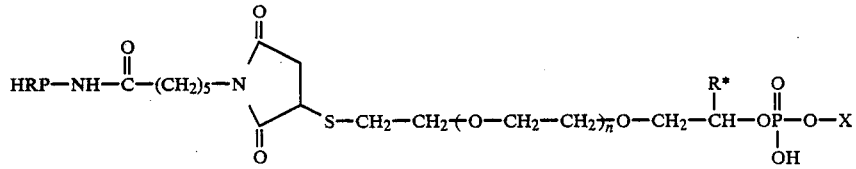

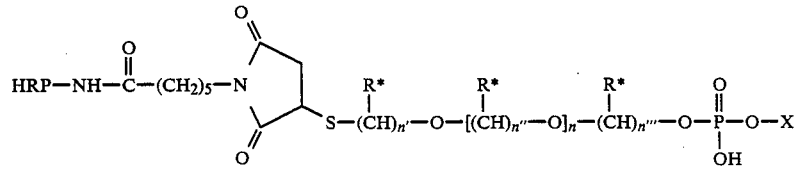

* * * * *